United States Patent [19]

Briggs

[11] 4,264,471

[45] Apr. 28, 1981

[54] SERUM AND PLASMA CLARIFICATION PROCESS

[75] Inventor: Anglis R. Briggs, Newark, Del.

[73] Assignee: E. I. Du Pont de Nemours and Company, Wilmington, Del.

[21] Appl. No.: 45,182

[22] Filed: Jun. 4, 1979

[51] Int. Cl.[3] .................... G01N 33/48; G01N 33/92

[52] U.S. Cl. .................... 252/408; 23/230 B; 23/909; 260/112 B

[58] Field of Search .............. 23/230 B, 909; 252/408; 260/112 R, 112 B

[56] References Cited

U.S. PATENT DOCUMENTS

| | | | |
|---|---|---|---|
| 3,682,835 | 8/1972 | Louderback | 23/909 X |
| 4,039,285 | 8/1977 | Teipel | 252/408 X |
| 4,096,136 | 6/1978 | Ayers et al. | 260/112 B |
| 4,185,963 | 1/1980 | Heuck | 23/230 B |

*Primary Examiner*—Arnold Turk

[57] ABSTRACT

A process for obtaining delipified human serum or plasma of low turbidity, and therefore decreased light scattering, is provided. This process comprises the simultaneous steps of deionization and pH adjustment of the serum or plasma to near the isoelectric point of lipoproteins commonly found in sera and results in the precipitation of much of the lipoprotein fraction. The process is carried out utilizing a mixed anion-cation exchange resin. The sera so obtained can be used as base material or a special diluent for verifying analytical information obtained in clinical analyses.

6 Claims, No Drawings

SERUM AND PLASMA CLARIFICATION PROCESS

DESCRIPTION

1. Technical Field

This invention relates to delipified human serum and more particularly to such serum and a process for its preparation utilizing a mixed anion-cation exchange resin.

2. Background Art

Sera of low turbidity and high optical clarity (low level of light scattering) are desirable for the preparation of serum based control materials.

Research Disclosure, Volume 162, No. 16229, October, 1977, describes a procedure for improving the optical clarity of freeze dried sera by incorporating sugar into them. The added sugar, however, results in a lower lyophilizing temperature, making that step more difficult.

Wolfson, et al., in the American Journal of Clinical Pathology, Volume 18, 273 (1948), describe a procedure for salting out lipoproteins from sera by the addition of 25% (weight/volume) of aqueous sodium sulfate. The addition of salts leads to difficulties described above and also to possible alteration in protein stereochemistry.

Finley, et al., in Clinical Chemistry, Volume 24, 931 (1978), report a procedure for removing lipoproteins from sera by the addition of mixtures of dextran and magnesium. This procedure also suffers from the above disadvantages and the additives need to be removed in certain circumstances.

A. Noma, et al., in Clinical Chemistry, Volume 24, 1504 (1978), describe a procedure for low density lipoprotein removal by the use of calcium ions and sodium heparin. An anion exchange resin is utilized to remove the added heparin.

Viikari, et al., in Clinical Chemistry, Volume 24, 174 (1978), describe a density gradient centrifugation procedure for the isolation of lipoproteins from sera. This procedure is not practically applicable to large volumes.

U.S. Pat. Nos. 3,928,566, issued Dec. 23, 1975 and 3,932,943, issued Jan. 20, 1976, both to A. R. Briggs, et al., disclose a serum base material of high optical clarity and its preparation. The process involves the rapid freezing of sera by spraying into a moving bath of fluorocarbon refrigerant followed by the lyophilization of the resultant frozen droplets. The high optical clarity of the sera, still containing lipoproteins, is apparently due to the fact that no lipoprotein precipitation occurs during the rapid freezing step.

U.S. Pat. No. 4,007,008, issued Feb. 8, 1977 to M. J. Becker, et al., discloses a method for treating animal blood to reduce enzyme activity and ion levels. The method involves the steps of sequentially raising the pH to above normal serum pH to denature the enzymes present then neutralizing the serum to terminate the enzyme activity reduction reaction followed by treatment with a mixed bed anion-cation ion exchange resin to reduce electrolyte level back to the original level. No lipoprotein is removed from the sera during this procedure.

There is a distinct need for delipified human serum or plasma of high optical clarity for the manufacture of serum based control material by efficient and economic methods.

DISCLOSURE OF THE INVENTION

The process for preparing substantially completely delipified animal, including human, serum or plasma comprises the steps of:

(A) rapid mixing of serum with a mixed anion-cation ion exchange resin, wherein the resin is present in a quantity sufficient to remove substantially all electrolytes from the serum and wherein there is sufficient excess of cation resin over anion resin to reduce the pH of the serum to $5.2 \pm 0.3$;

(B) continued mixing until the pH reaches a value of $5.2 \pm 0.3$; and (C) separation of the supernatant serum resulting after mixing is discontinued and the resin and a precipitate formed during steps (A) and (B) are allowed to settle.

DESCRIPTION OF THE INVENTION

The process for delipification of this invention is applicable to animal, including human, serum or plasma. For the sake of simplicity only the term serum will be used, although this disclosure is intended to encompass both serum and plasma.

By serum is meant the cell-free liquid portion of blood remaining after clot formation and removal (factors involved in clotting are removed, i.e., fibrin). Serum is prepared as follows:

Whole blood is withdrawn from the body into a suitable container such as a test tube and kept undisturbed. Within a few minutes clot formation occurs. The blood sample can then be centrifuged to compact the clot and squeeze out the fluid serum or can be kept for several hours during which time the clot slowly contracts and squeezes out the serum. The serum can then be separated from the clot by simple decantation.

By plasma is meant the cell-free liquid portion of blood which has been prevented from clotting by the use of anti-coagulants (clotting factors still remain). Plasma is prepared as follows. Whole blood is withdrawn from the body into a container which also contains anti-coagulant. Blood anti-coagulants often used are: heparin, oxalates, citrates, fluorides, and EDTA. All of these, except heparin, act by binding the calcium ion normally found in the blood and thereby inhibiting the clotting mechanism. Heparin inhibits the activation of prothrombin to thrombin and therefore prevents the thrombin-induced conversion of fibrinogen to fibrin. The whole blood is centrifuged or permitted to stand undisturbed to pack the blood cells or allow them to settle. The plasma is then separated from the cells.

The present process results in greatly decreased levels of lipoproteins in sera thereby eliminating the insoluble particles formed during lyophilization which cause unacceptable turbidity upon reconstitution. Optically clear (diminished light scatter) aesthetically pleasing serum base materials, useful for the formulation of control materials, result.

It has been found unexpectedly that mixing specially formulated mixed anion-cation ion exchange resin with serum under carefully controlled pH conditions, which include the lowering of the pH to $5.2 \pm 0.3$, results in an optically clear delipified human serum from which low molecular weight ionized species (salts) have also been removed.

The ion exchange resins can be strong acid-strong base or weak acid-weak base combinations. In either case, they are in the $H^+$ and $OH^-$ forms, respectively.

Two factors in determining the amount of mixed ion exchange resin to be utilized must be carefully controlled to achieve the desired properties for the delipified sera. The first factor is the level of cations and anions present in the serum to be treated. Sufficient resin is necessary for substantially complete exchange of anions and cations.

The second factor is controlled by the final pH value to which the serum needs to be reduced. This pH value is the isoelectric point of the lipoproteins usually found in sera. (The isoelectric point is defined by Hackh's Chemical Dictionary, Third Edition, 1944, The Blakiston Company, Edited by J. Grant, page 454, as the point of electric neutrality or zero potential, meaning the pH value at which a substance such as a lipoprotein is neutral.)

The calculation for sufficient resin for the substantially complete exchange of ions is carried out based on the exchange capacity of the anion and cation ion exchange resins. Values of exchange capacity are determined by a titrimetric procedure as described, for example, in Dowex: Ion Exchange, a bulletin of The Dow Company, 1958, 1959. For a sample calculation see the Example below.

To achieve the above-mentioned pH reduction, causing the precipitation of the lipoproteins from the sera simultaneously with the ion exchange, excess cation resin needs to be incorporated into the mixed anion-cation resin. The excess amount is determined by titrating a given volume, e.g., 25 ml, of serum with dilute (1.00 N) hydrochloric acid to a pH of 5.0. The required volume of the acid is designated as serum titration value and the corresponding amount of cation exchange resin, in equivalents, is utilized in addition to the theoretical amount needed for ion exchange.

Generally, frozen human serum is used for the process of the invention. It is allowed to thaw, preferably rapidly at 32°-37° C. in a water bath (see Szasz, Clinical Chemistry, Volume 24, 1557 (1978). The serum is inspected to ascertain that no visible lipemia or hemolysis occurred, i.e., that the serum is clear and substantially colorless. Visibly red or pink serum or turbid serum is not acceptable for the present process because such serum would not be useful as base material for control products. Also, for safe handling in the laboratory, the serum should be non-pathogenic (HAA and VDRL negative).

During the mixing of the ion exchange resin and serum, the pH changes occurring need to be monitored. The initial pH increases to approximately 9.0-10.3 in the first few minutes after the addition of the resin to the serum. To complete the desired pH reduction and ion removal, excess mixed resin is usually necessary to allow for reduced resin efficiency caused by lipoprotein deposition on the resin beads during its precipitation. Approximately 1.45±0.15 times the calculated theoretical amount of mixed resin may be needed.

After a pH of 5.2±0.3 has been reached (usually 8-15 minutes total time), mixing is discontinued and the supernatant serum is separated from the resin and the precipitated lipoproteins. Separation can be effected by any of the customary means such as filtration, decantation, pumping of the supernatant serum, etc.

The pH of the separated serum can be further adjusted to a value of 4.0±1.0 with hydrochloric acid to insure low residual levels of enzyme activity in the serum. It is desirable that, for example, creatine kinase (CK) activity be reduced to not more than 3 IU/liter. To achieve this, the serum is held at a pH of approximately 4.0±0.2 for a sufficient length of time to substantially complete the denaturation process. This can be monitored by assaying for CK activity.

The serum can be stored overnight at the final pH if stored at approximately 4° C. but, preferably, the pH is adjusted to its final value of 7.3±0.3 with a buffer such as 2-amino-2-hydroxymethyl-1,3-propanediol. This delipified serum can be stored indefinitely in the frozen state or at 4° C. for approximately 48 hours (without the addition of microbial inhibitors).

The serum resulting from the process of this invention can be utilized to prepare control products for clinical analysis such as by the addition of predetermined amounts of purified CKMB isoenzyme. The resultant material can be lyophilized, affording optically clear control materials upon reconstitution, to preserve enzymatic activity. The lyophilized material can be reconstituted with water and can be diluted with delipified sera produced by the instant process at the appropriate time to be used as a control material.

EXAMPLE

A. Preparation of Mixed Anion-Cation Ion Exchange Resin

A general purpose, high capacity, strong acid (cation) exchange resin (Duolite GPC-301, available from the Diamond Shamrock Corporation) and a general purpose, high porosity, strong base (anion) exchange resin (Duolite GPA-316, available from the Diamond Shamrock Corporation) are blended. The amounts necessary are calculated as follows Manufacturers supply the exchange capacity of each resin on a dry weight basis. Since these resins are supplied prehydrated and the moisture content is variable, the exchange capacity is determined on the wet weight basis to allow proper formulation. The procedure described below was modified from the procedure outlined in Dowex: Ion Exchange, The Dow Company (1958, 1959).

Determination of exchange capacity of each prehydrated resin:

Cation: Add 25 g cation resin (GPC-301) to 250 ml of 1.0 N NaCl solution and while mixing titrate to neutrality (pH 7.00±0.05) with 2.5 N NaOH using a calibrated pH meter to monitor the pH. For a particular lot of this resin, 25 ml of NaOH was needed.

$$\text{exchange capacity} = \frac{OH^- \text{ consumed (meq)}}{\text{resin weight (g)}} = \frac{62.5 \text{ meq}}{25 \text{ g}} = 2.5 \text{ meq } H^+/\text{g resin.}$$

Anion: Add 25 g anion resin (GPA-316) to 250 ml of 1.0 N NaCl solution and while mixing titrate to neutrality (pH 7.00±0.05) with 2 N HCl using a properly calibrated pH meter to monitor the pH. For a particular lot of this resin, 16.25 ml HCl was needed.

$$\text{exchange capacity} = \frac{H^+ \text{ consumed (meq)}}{\text{resin weight (g)}} = \frac{32.5 \text{ meq}}{25 \text{ g}} = 1.3 \text{ meq } OH^-/\text{g resin.}$$

Determination of the resin ratio in the mixed resin:

In addition to having sufficient cation and anion resins to remove the electrolytes from the serum, extra cation resin is needed to exchange $H^+$ ions to reduce the resulting product to pH 5.2±0.3 (isoelectric point of lipoproteins). This amount, the serum titration value, is determined as follows: Titrate 25 ml of human serum to pH 5.0 with 1.0 N HCl (the average range for human serum is 35–45 ml). A particular lot of human serum had a serum titration value of 41 ml. This serum titration value (in milliequivalents) is equal to the additional cation exchange resin needed.

Formulation of the mixed resin:

Since theoretical exchange capacity is needed and since human serum usually contains approximately 150 meq/liter of each of cations and anions, 191 meq/liter (150 meq+41 meq) of cation exchange resin and 150 meq/liter of anion exchange resin are needed. Of the particular lot of resins utilized, one needs (191 meq/liter)/(2.5 meq/g)=76 grams of cation exchange resin/liter of serum and (150 meq/liter)/(1.3 meq/g)=115 grams of anion exchange resin/liter of serum.

The two resins are thoroughly mixed in a commercial blender and can be stored in sealed containers to prevent drying out and any reaction with atmospheric carbon dioxide.

B. Preparation of Human Serum

The yield of delipified serum in the present process is approximately 80–85% of the starting volume and therefore approximately 1.25 times the amount of final serum needed is removed from frozen storage.

The serum is thawed rapidly in a water bath kept at between 32°–37° C. although for large volume preparations overnight thawing is permissible. After inspection of the thawed serum for unacceptable signs of color (lipemia) and turbidity (hemolysis), the serum is placed in a polyethylene tank of sufficient size to provide space for the mixed resin to be added and to allow for vigorous stirring with an overhead mixer.

C. Preparation of Delipified Serum

Into a volume of 32 liters of thawed serum having a pH of 7.5–8.0 and showing no pink or red color or turbidity is added 8.96 kilograms of the mixed ion exchange resin prepared in (A) above with rapid mixing. The pH changes occurring during the exchange reaction are monitored by an electrode placed in the reaction tank and attached to an accurately calibrated pH meter.

After the pH reaches 10.1 (in 1.5 minutes), it begins to decrease slowly and reaches 5.15 in a total elapsed time of 12 minutes).

After this 12-minute period the resin and the precipitated lipoproteins are allowed to settle and the supernatant delipified serum is removed by pumping.

The pH of the serum is adjusted to 7.3 with the above amine, requiring approximately 74 grams. This pH adjustment must be done with care to insure that the pH does not rise above the desired value. Since the powdered amine dissolves in the serum only slowly, good mixing during its addition is important.

The delipified serum can be stored at 4° C. for approximately 48 hours; if longer storage is required, it should be in the frozen stage to avoid microbial growth.

D. Completion of Enzyme Denaturation

The pH of the supernatant serum prepared as in (C) above is adjusted to 4.0±0.2 using 89 ml of 6 N HCl and maintained at this pH for one hour. At this time a 25 ml sample is removed, its pH is adjusted to 7.3 with powdered 2-amino-2-hydroxymethyl-1,3-propanediol and assayed for residual CK activity, showing a value of 1 IU/liter.

After the residual CK activity has been reduced to the desired level, the pH of the serum is adjusted to 7.3 with the above amine, requiring 112 grams. This pH adjustment must be done with care to insure that the pH does not rise above the desired value. Since the powdered amine dissolves in the serum only slowly, good mixing during its addition is important. The delipified serum can be stored at 4° C. for approximately 48 hours; if longer storage is required, it should be in the frozen stage to avoid microbial growth.

E. Preparation of Control Material

Into 5 liters of the serum prepared in step (D) above is added 1250 IU of purified CKMB isoenzyme at room temperature. The isoenzyme is isolated according to the procedures outlined by known methods, see for example, D. Mercer, Clinical Chemistry, Volume 20, 36 (1974), L. G. Morin, Clinical Chemistry, Volume 22, 92 (1976), and S. Rosalki, Clinical Chemistry, Volume 22, 1753 (1976).

The control material so prepared, having a defined enzymatic activity, can be lyophilized to preserve this enzymatic activity until the reconstituted solution is utilized as a control material for clinical analyses for CKMB. The reconstituted material can be diluted to various concentration levels with the delipified serum obtained by the process of this invention.

I claim:

1. A process for preparing substantially completely delipified animal serum comprising the steps of:

(A) rapid mixing of serum with a mixed anion-cation ion exchange resin, wherein the resin is present in a quantity sufficient to remove substantially all electrolytes from the serum and wherein there is sufficient excess of cation resin over anion resin to reduce the pH of the serum to 5.2±0.3;

(B) continued mixing until the pH reaches a value of 5.2±0.3; and (C) separation of the supernatant serum resulting after mixing is discontinued and the resin and a precipitate formed during steps (A) and (B) are allowed to settle.

2. The process of claim 1 wherein the animal serum is human serum.

3. The process of claim 1 wherein the anion exchange resin is a strong base resin and the cation exchange resin is a strong acid resin.

4. The process of claim 1 wherein the anion exchange resin is a weak base resin and the cation exchange resin is a weak acid resin.

5. The process of claim 1 wherein after step (C) the pH of said serum is adjusted to a pH of 7.3±0.3.

6. The process of claim 5 wherein the pH is adjusted with 2-amino-2-hydroxymethyl-1,3-propanediol.

* * * * *